(12) United States Patent
Bowman et al.

(10) Patent No.: US 7,244,235 B2
(45) Date of Patent: Jul. 17, 2007

(54) SPLIT-NIGHT SLEEP DIAGNOSTIC SYSTEM (75) Inventors: Bruce R. Bowman, Eden Prairie, MN (US); Gary L. Hansen, Eden Prairie, MN (US)

(73) Assignee: Mallinckrodt, Inc., St. Louis, MO (US)

( * ) Notice: Subject to any disclaimer, the term of this patent is extended or adjusted under 35 U.S.C. 154(b) by 225 days.

(21) Appl. No.: 10/283,356

(22) Filed: Oct. 30, 2002

(65) Prior Publication Data
US 2004/0087866 A1    May 6, 2004

(51) Int. Cl.
*A61B 5/08* (2006.01)
*A61M 16/00* (2006.01)
*A62B 7/00* (2006.01)
*F16K 31/02* (2006.01)

(52) U.S. Cl. ............ 600/529; 128/200.24; 128/204.18; 251/129.01

(58) Field of Classification Search ............ 128/204.18–205.25; 600/529–543; 604/32
See application file for complete search history.

(56) References Cited

U.S. PATENT DOCUMENTS

| | | | | |
|---|---|---|---|---|
| 2,754,819 A | * | 7/1956 | Kirschbaum | 128/204.23 |
| 5,438,981 A | * | 8/1995 | Starr et al. | 128/205.24 |
| 5,490,502 A | * | 2/1996 | Rapoport et al. | 128/204.23 |
| 5,503,146 A | * | 4/1996 | Froehlich et al. | 128/204.23 |
| RE35,339 E | * | 10/1996 | Rapoport | 128/204.18 |
| 5,560,354 A | * | 10/1996 | Berthon-Jones et al. | 128/205.25 |
| 5,598,838 A | * | 2/1997 | Servidio et al. | 128/204.23 |
| 5,694,923 A | * | 12/1997 | Hete et al. | 128/204.18 |
| 5,885,211 A | * | 3/1999 | Eppstein et al. | 600/309 |
| 6,189,532 B1 | * | 2/2001 | Hely et al. | 128/205.24 |
| 6,443,154 B1 | * | 9/2002 | Jalde et al. | 128/205.29 |
| 6,745,770 B2 | * | 6/2004 | McAuliffe et al. | 128/205.24 |

* cited by examiner

*Primary Examiner*—Charles A. Marmor, II
*Assistant Examiner*—Patricia C. Mallari
(74) *Attorney, Agent, or Firm*—Baker Botts L.L.P.

(57) ABSTRACT

A split-night sleep diagnostic system is provided for diagnosing and treating sleep apnea in a single night. The diagnostic system includes a blower, a respiratory interface and a conduit connected between the blower and the respiratory interface. Also included is a valve disposed along the conduit. The valve includes an aperture formed in the conduit between the blower and the respiratory interface, and a valve member movable between a first position partially occluding the conduit so that air flows through the aperture and a second position blocking the aperture so that continuous positive airway pressure is provided to a patient. Both diagnosis and titration can be performed using a single system at a single location over the course of a single night.

34 Claims, 6 Drawing Sheets

SPLIT-NIGHT SLEEP DIAGNOSTIC SYSTEM

BACKGROUND OF THE INVENTION

1. Field of the Invention

The present invention relates generally to a method and an apparatus for treating apnea and, more particularly, to a method and an apparatus for diagnosing and treating sleep apnea in a single night.

The term "apnea", as used herein, is meant to encompass any type of breathing disorder, for example, apnea (complete cessation of breathing), patency obstruction, partial obstruction, apnea that arises in patients with various cardiac, cerebrovascular and endocrine conditions unrelated to the state of the upper airway, or the like.

2. Description of the Background Art

Sleep apnea arises during sleep when a patient undergoes repeated cessation of breathing. The cessation is caused by an obstruction of the throat air passage. Repeated cessation of breathing reduces blood oxygen and disturbs sleep. Reduction of blood oxygen can cause heart attacks and strokes, while sleep disturbances or fragmentation can produce excessive daytime sleepiness.

Treatment of sleep apnea typically occurs in two stages: assessment (diagnosis) and titration. In the first stage, the patient is monitored for signs of disordered breathing. In the second stage, the patient wears a continuous positive airway pressure (CPAP) mask. The CPAP mask covers the nose of the patient and forms a pressure seal with the surrounding face. While the patient sleeps, air pressure in the mask is slowly increased until signs of apnea cease.

In the past, the two stages occurred in a specialized hospital sleep center on two consecutive nights. More recently, both stages occur in a single night, the so-called "split night" method. In such cases, however, both stages are performed in a hospital sleep center.

Recent clinical results have shown the value of conducting diagnostic testing (assessment) in the home, and portable diagnostic devices are now available for this purpose. Advantages include lower cost, increased comfort of the patient, and a more realistic assessment of sleep patterns under normal home conditions. However, the patient still needs to return to a hospital sleep center for titration.

An "auto-CPAP" device is capable of performing titration on a patient who has already been diagnosed. Such devices monitor a limited range of physiologic variables and attempt to set the pressure in the CPAP mask to an optimal value. In other words, the minimum level of pressure (i.e., titration pressure) required to produce a patent pharyngeal airway or the necessary therapeutic pressure required for properly treating the patient is determined. Some clinicians have sought to use the auto-CPAP device as a substitute for conventional sleep studies. However, the severity of the illness in the absence of CPAP pressure is never determined. Even if the auto-CPAP device can accurately determine the titration pressure, no baseline exists for comparing to standard diagnostic criteria.

While the aforementioned auto-CPAP device is an improvement over the conventional CPAP device, there continue to be a need in the art for an improved diagnostic method and system for diagnosing and treating sleep apnea in a single night, preferably in the home.

SUMMARY OF THE INVENTION

A first aspect of the invention is generally characterized in a diagnostic system for diagnosing and treating sleep apnea in a single night. The system comprises a blower, a respiratory interface and a conduit connected between the blower and the respiratory interface. Also included is a valve disposed along the conduit. The valve comprises an aperture formed in the conduit between the blower and the respiratory interface, and a valve member movable between a first position partially occluding the conduit so that air flows through the aperture and a second position blocking the aperture so that continuous positive airway pressure is provided to a patient. A signal line is connected between a controller and the valve for conveying signals therebetween and allowing the controller to control the operation of the valve.

Another aspect of the present invention is generally characterized in a device usable with an existing continuous positive airway pressure (CPAP) system for modifying the operation of the CPAP system. The CPAP system comprises a conduit connected between a blower and a respiratory interface. The device comprises a valve disposed along the conduit. The valve includes an aperture formed in the conduit between the blower and the respiratory interface, and a valve member movable between a first position partially occluding the conduit so that air flows through the aperture and a second position blocking the aperture so that continuous positive airway pressure is provided to a patient.

Yet another aspect of the present invention is generally characterized in a method of diagnosing and treating sleep apnea in a single night using a system having a conduit with a valve. The method includes the steps of monitoring a patient's breathing with the valve open for a first portion of the night, and providing continuous positive airway pressure with the valve closed for a second portion of the night.

The above and other features and advantages of the present invention will be further understood from the following description of the preferred embodiments thereof, taken in conjunction with the accompanying drawings wherein like reference numerals are used throughout the various views to designate like parts.

DETAILED DESCRIPTION OF THE PREFERRED EMBODIMENTS

Figure 1:
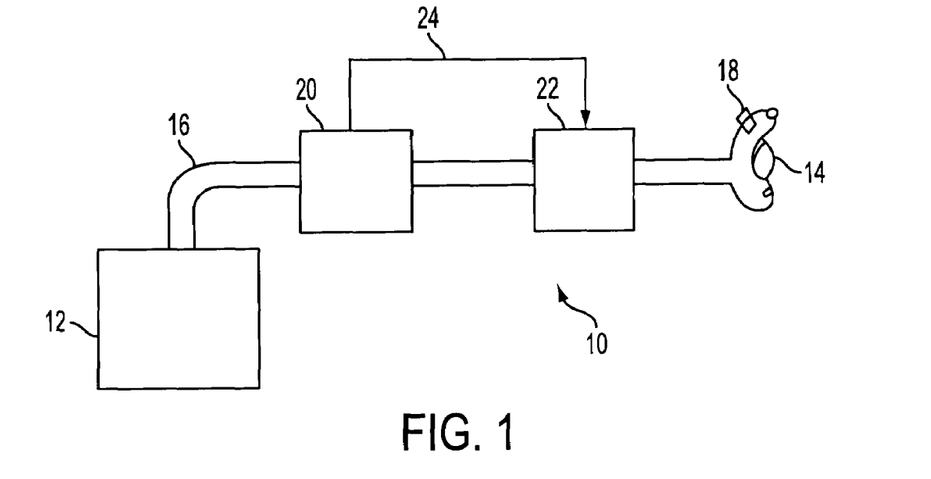
FIG. 1 is a schematic diagram showing an embodiment of a system for diagnosing and treating sleep apnea according to the present invention.

An embodiment of a split-night sleep diagnostic system 10 according to the present invention is shown in FIG. 1. The diagnostic system 10 can be portable and suitable for use in a patient's home. The diagnostic system 10 is also suitable in any environment as desired. The diagnostic system 10 generally includes a fan or blower 12 and a breathing mask 14 connected by a gas supply hose 16. The mask 14 is configured to deliver a breathing gas to the nose and mouth of a patient, and is shown with an optional vent 18 for purging expired respiratory gases. The blower 12 is configured to supply a therapeutically effective flow of breathing gas to the mask 14 via the hose 16 such that a continuous positive pressure is maintained in the patient's airway. The blower 12, breathing mask 14 and hose 16, as thus far described, form a conventional continuous positive airway pressure (CPAP) system for treating sleep apnea. As details of conventional CPAP systems are available in numerous publications and patents including, by way of example, U.S. Pat. Nos. 5,645,053, 5,645,054, 5,881,724 and 5,901,704, no attempt is made herein to provide a detailed description of such systems or these components.

In accordance with the present invention, a controller 20 and a valve 22 are interposed between the blower 12 and the breathing mask 14 to modify operation of the CPAP system so that diagnosis and titration can be performed using a single system at a single location over the course of a single night. Existing CPAP devices can be implemented with the controller 20 and the valve 22, or, alternatively, the devices may include dedicateduse devices.

Titration can be controlled internally by the blower 12 or externally by the controller 20. The CPAP system can be designed to include an internal controller, or, alternatively, a separate controller can be used with any CPAP system. The controller need not interact with the CPAP since the only function of the controller would be to close the valve about half way through the night. However, the controller may provide a single logical "on-off" report of its state to the CPAP system, or the CPAP system may provide an "on-off" command to the controller. Since the CPAP system logs or maps pressure and airflow versus time, the point at which the valve closes can be indicated on the report.

Referring to FIG. 1, the controller 20 and the valve 22 are shown at spaced locations along the length of the hose 16 but can be positioned anywhere between the blower 12 and the mask 14. Preferably, the valve 22 is located downstream of the controller 20 as shown. A signal line 24 is connected between the controller 20 and the valve 22 to convey signals therebetween allowing the controller 20 to control operation of the valve 22. The configuration of the signal line 24 is dependent upon the type of valve employed. For example, if the valve is electrically actuated, the signal line can include electrical conductors, or, if actuation is pneumatic, the signal line can include an air hose.

Figure 2:
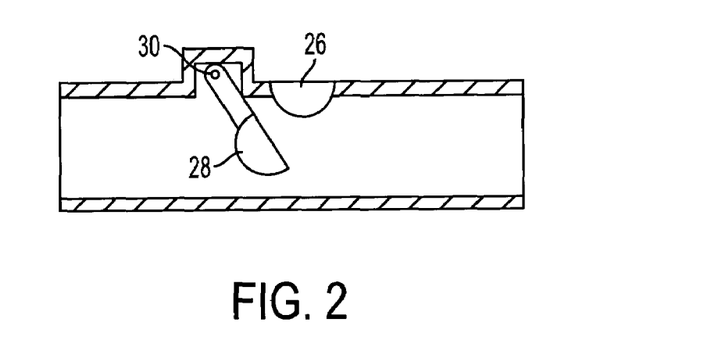
FIG. 2 is a fragmentary sectional view of the diagnostic system of FIG. 1 showing a valve in an open state.
Figure 3:
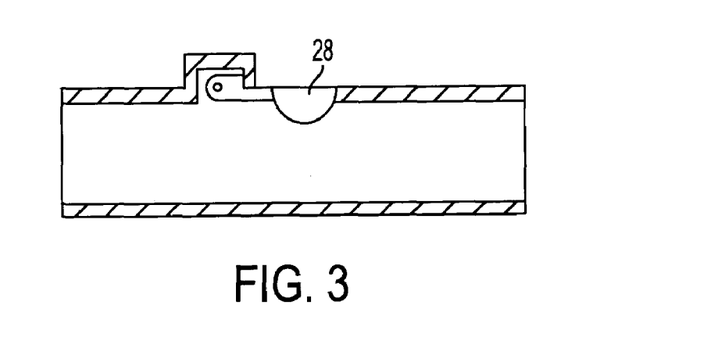
FIG. 3 is a fragmentary sectional view of the diagnostic system of FIG. 1 showing the valve in a closed state.

A first embodiment of a valve 22 for use in a split-night diagnosis system 10 according to the present invention is shown in FIGS. 2 and 3. The valve 22 is composed of an aperture 26 formed in the hose 16 and a valve member 28 movable within the hose 16 between open and closed positions by means of an actuator (not shown). The valve member 28 is shown as a flap mounted on a pivot 30. In the open position, as shown in FIG. 2, the valve member 28 is angularly spaced from the aperture 26 thereby partially occluding the hose 16 while permitting air to flow through the aperture 26. In the closed position, as shown in FIG. 3, the valve member 28 covers the aperture 26 to allow unimpeded gas flow through the hose 16 while preventing air from flowing through the aperture 26 within the hose 16 by means of an actuator (not shown).

In the open position, the diagnostic system 10 is in the assessment stage. The CPAP system does not provide therapeutic levels of pressure or breathing gas to the patient. Rather, the patient receives normal air at atmospheric pressure (i.e., a non-pressurized air supply) for the first half of the night. In the closed position, the diagnostic system 10 is in the titration stage. The CPAP system provides therapeutic levels of pressure to the patient, and the patient receives treatment for the second half of the night.

In the preferred embodiment, the valve member 28 is configured so that while in the open position, the air flow rate completely purges expired respiratory gases released from the patient and does not exceed the capacity of the blower 12 to regulate pressure. Typically, the air flowing past the valve member 28 is at least 10 L/min at >3 cm $H_2O$ CPAP pressure under static conditions (i.e., between breaths).

The aperture 26 is configured so that released pressure created within the mask 18 by the patient does not exceed a predetermined value. The value is selected so that the pressure does not inadvertently erase the signs of apnea which need to be treated or diagnosed. The threshold value should be less than 1 cm $H_2O$.

In the preferred embodiment, the valve member 28 has a circular hole equal to 0.313 inches in diameter, and the aperture 26 is equivalent to a circular hole equal to 0.61 inches in diameter. The valve member 28 and the aperture 26, however, are not limited to a specific geometry and size, respectively. As long as, in the open position, the valve member 28 and the aperture 26 meet certain criteria, the valve member 28 can have any geometry and the aperture 26 can be any size. For example, the aperture 26 must be large enough such that maximum pressure in the mask 18 is less than 1–2 cm $H_2O$ during the peak of expiratory flow. The airflow resistance of the valve member 28 must be high enough such that the CPAP device contributes little or no excess pressure to the mask 18 (e.g., the resistance of the valve member 28 is slightly higher than the resistance of the aperture 26). The airflow resistance of the valve member 28 must be low enough such that the combined exhaust flow from the aperture 26 and vent 18 is sufficient to clear all expiratory gases that may have built up within the mask 18 and hose 16. Further, the airflow from the aperture 26 should not annoy the patient (e.g., by impinging on the skin or being excessively noisy).

Figure 4:
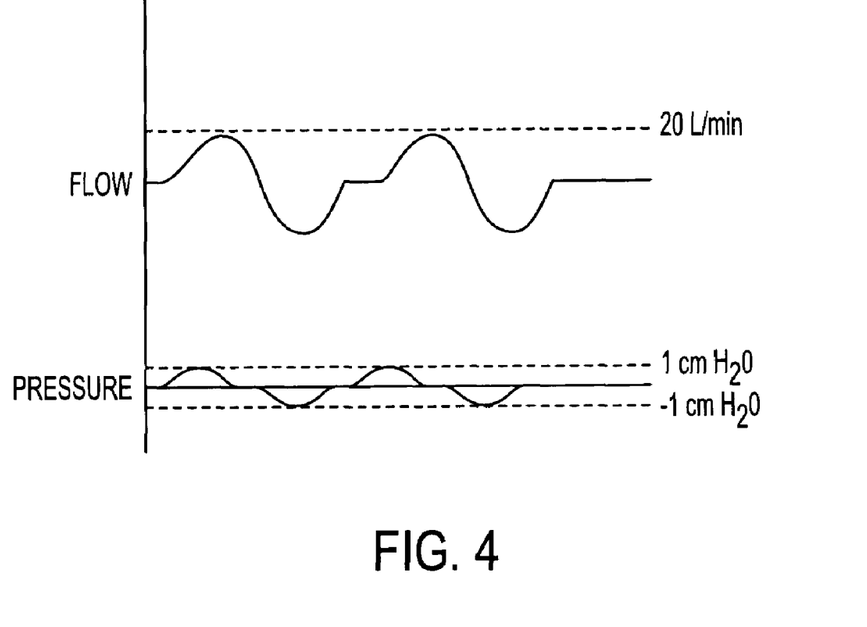
FIG. 4 is a graph showing gas flow and pressure over time for the diagnostic system of the present invention when the valve member is in the open state.
Figure 5:
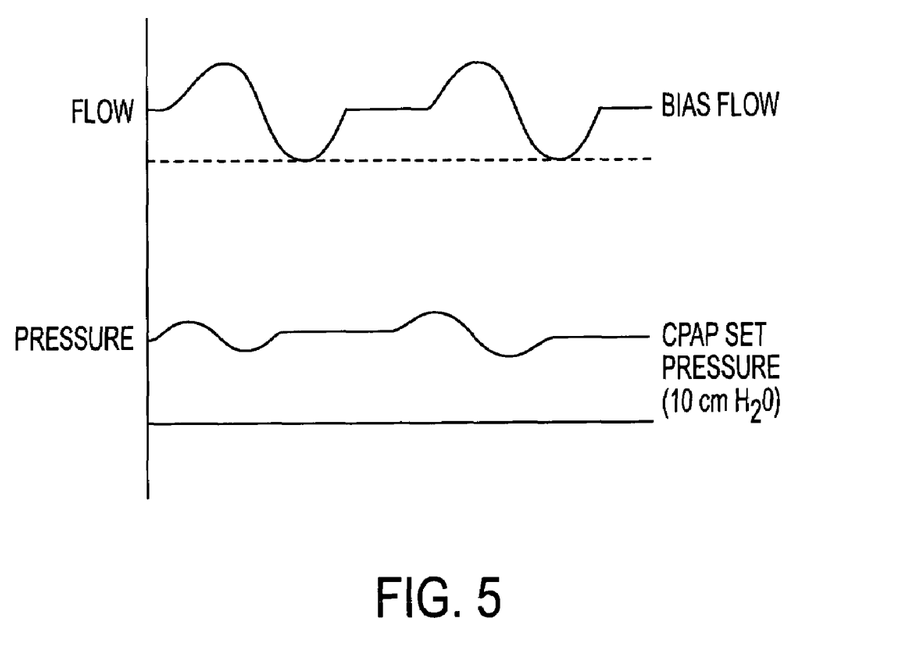
FIG. 5 is a graph showing gas flow and pressure over time for the diagnostic system of the present invention when the valve member is in the closed state.

FIG. 4 is a graph showing gas flow in the valve 22 and pressure at the mask 14 over time when the valve member 28 is in the open position. Peak-to-peak flow rates are approximately ±20 L/min, centered about zero flow between breaths. The pressure in the mask 14 never varies far from zero (i.e., atmospheric). FIG. 5 is a graph showing gas flow in the valve 22 and pressure at the mask 14 over time when the valve member 28 is in the closed position. The peak-to-peak flow rates are unchanged, however, there is a slight positive bias due to the purged expired respiratory gases through the vent 18. The CPAP system thus regulates the pressure in the mask 14, which does not vary from the predetermined pressure (of the CPAP system).

Figure 6:
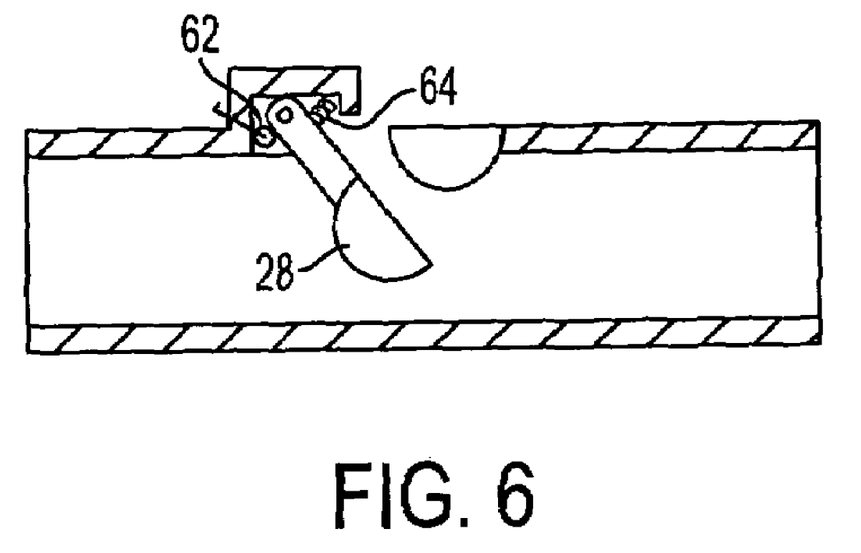
FIG. 6 is a fragmentary sectional view of another valve for use in the diagnostic system according to the present invention.

Another embodiment of a valve 22 for use in the diagnosis system 10 according to the present invention is shown in FIG. 6. The valve in this embodiment is similar to the valve described in conjunction with FIGS. 1 and 2; however, the valve member 28 is movable within the hose 16 between open and closed positions by pneumatic actuation. The signal line 24 of FIG. 1 may contain an air hose (not shown), or an expandable air bladder 62 may contain an air deliver hose, in which a pump/vacuum may be drawn through the air bladder 62 in order to inflate or deflate the air bladder 62. As best seen in FIG. 6, the valve member 28 is located between the air bladder 62 and a spring 64. When the air bladder 62 is deflated, the spring 64 is extended such that the valve member 28 is moved to the open position. When the air bladder 62 is inflated, the spring 64 is compressed such that the valve member 28 is moved to the closed position.

Figure 7:
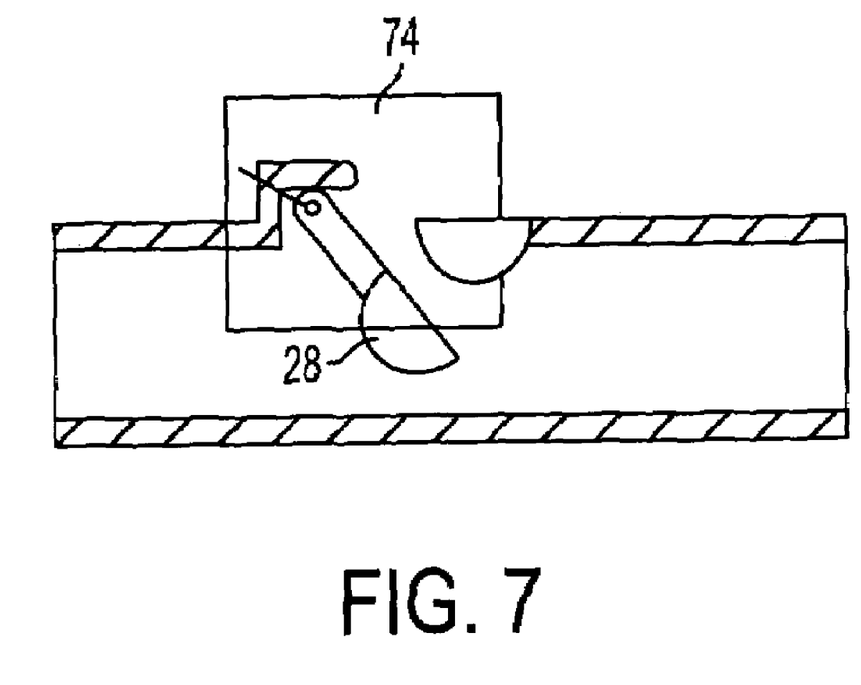
FIG. 7 is a fragmentary sectional view of yet another valve for use in the diagnostic system according to the present invention.

FIG. 7 is a fragmentary sectional view of yet another valve for use in the diagnosis system 10 according to the present invention. The valve in FIG. 7 is similar to the valve described in conjunction with FIG. 1; however, the valve member 28 is movable within the hose 16 between open and closed positions by solenoid actuation. In this case, the valve member 28 rotates about a longitudinal axis via a rotary solenoid 74. By way of example, the rotary solenoid 74 can employ return springs on the return stroke of a solenoid to return the valve member 28 to its initial resting position upon deenergization of a solenoid coil.

Figure 8:
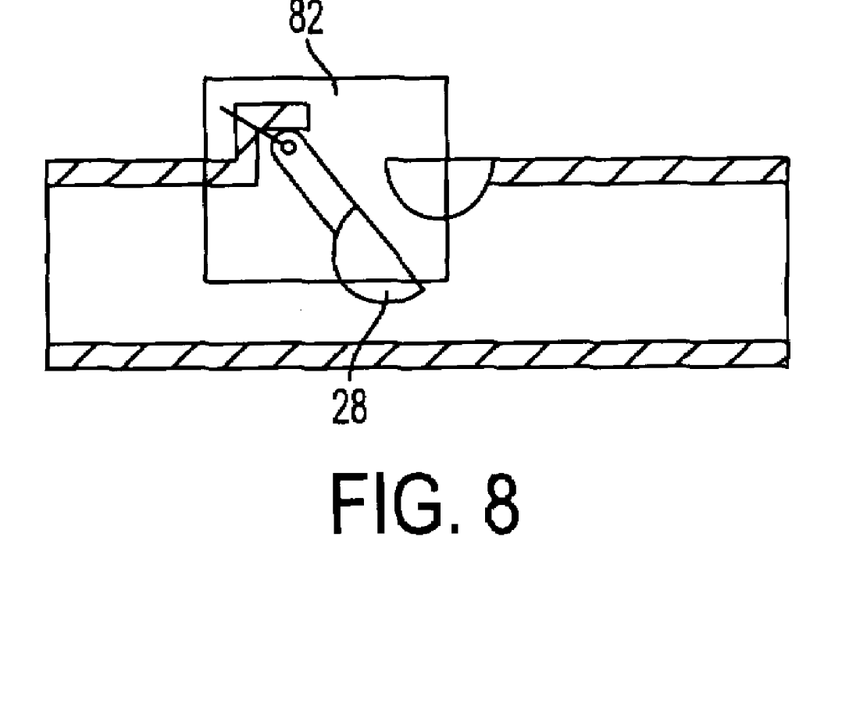
FIG. 8 is a fragmentary sectional view of still another valve for use in the diagnostic system according to the present invention.

FIG. 8 is a fragmentary sectional view of still another valve for use in the diagnosis system 10 according to the present invention. The valve in FIG. 8 is similar to the valve described in conjunction with FIG. 1; however, the valve member 28 is movable within the hose 16 between open and closed positions by motor actuation. Here, the valve member 28 rotates about a longitudinal axis via a motor 82.

Figure 9:
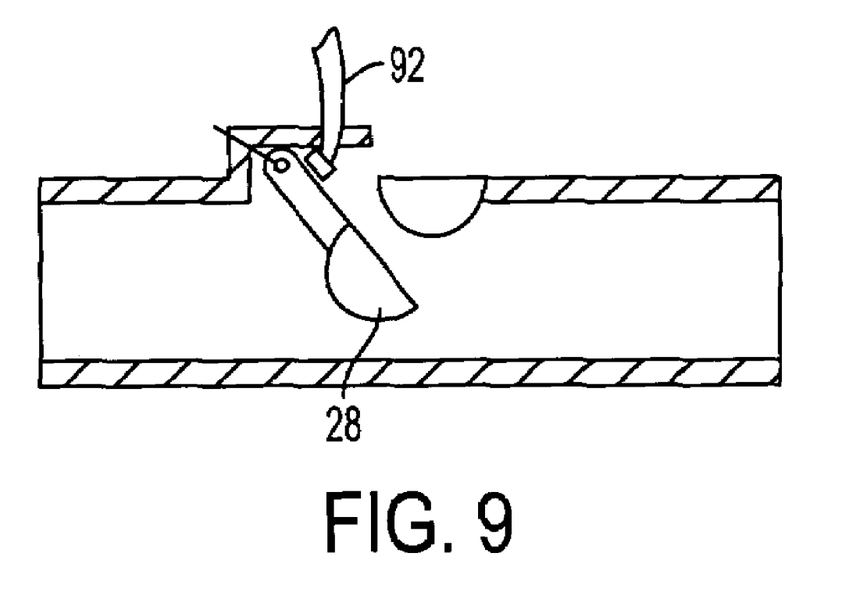
FIG. 9 is a fragmentary sectional view of a further valve for use in the diagnostic system according to the present invention.

A further embodiment of a valve for use in the diagnosis system 10 according to the present invention is shown in FIG. 9. In this embodiment, the valve member 28 is movable within the hose 16 between open and closed positions by electromagnetic actuation. Electromagnets 92 are disposed, for example, above and below the valve member 28. The electromagnets 92 exert electromagnetic forces on the valve member 28 in the open and closed positions. Although one electromagnet is shown in the drawing, more than one electromagnet can be used.

The valves 22 shown in FIGS. 6 through 9 are advantageous in that they can be incorporated into any new or existing CPAP system. While the valve member 28 is actuated via the above means, it will be appreciated that other means of actuating the valve member 28 are possible.

Figure 10A:
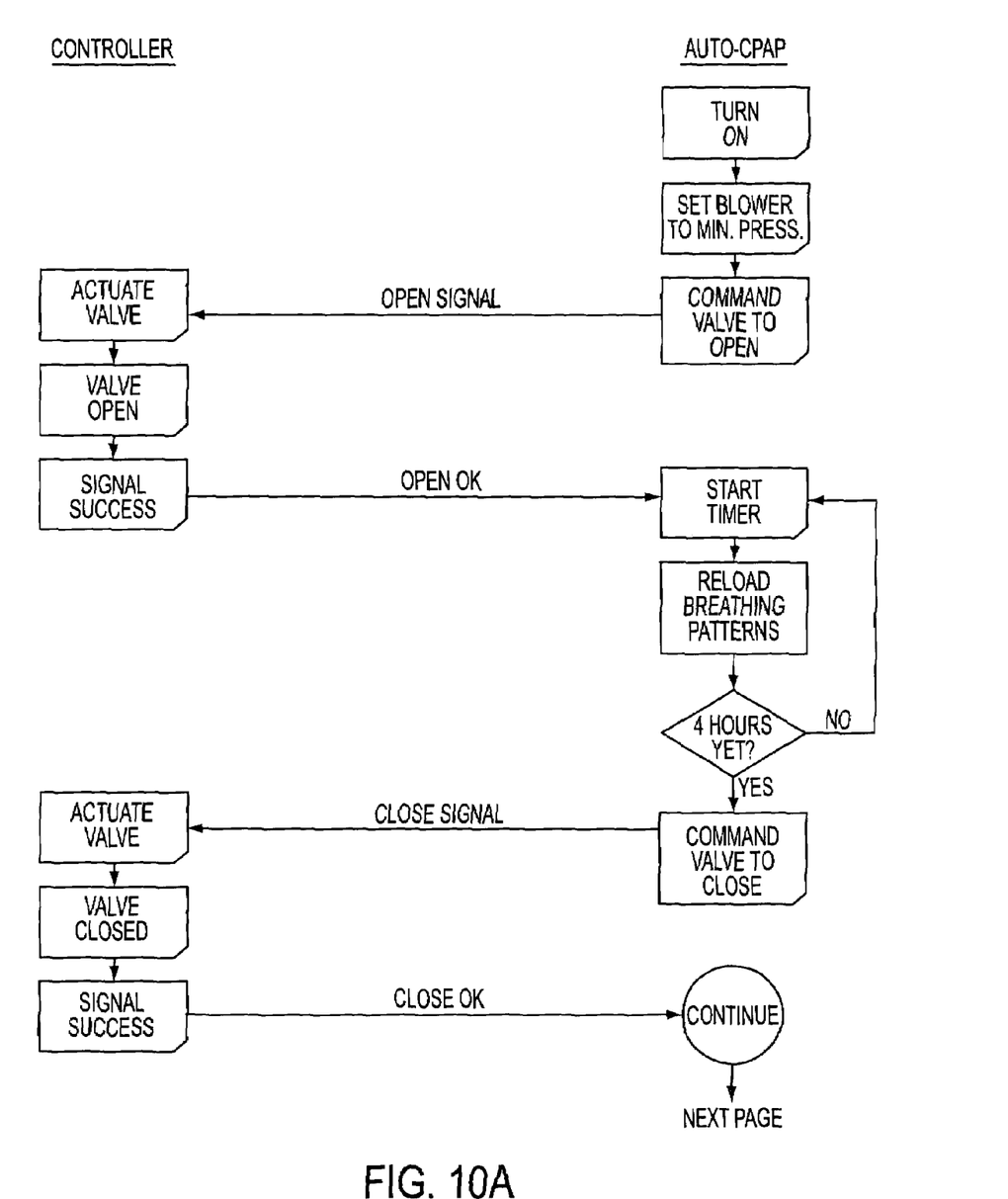
FIGS. 10A through 10B show a general flow chart of the overall operation of a preferred embodiment.
Figure 10B:
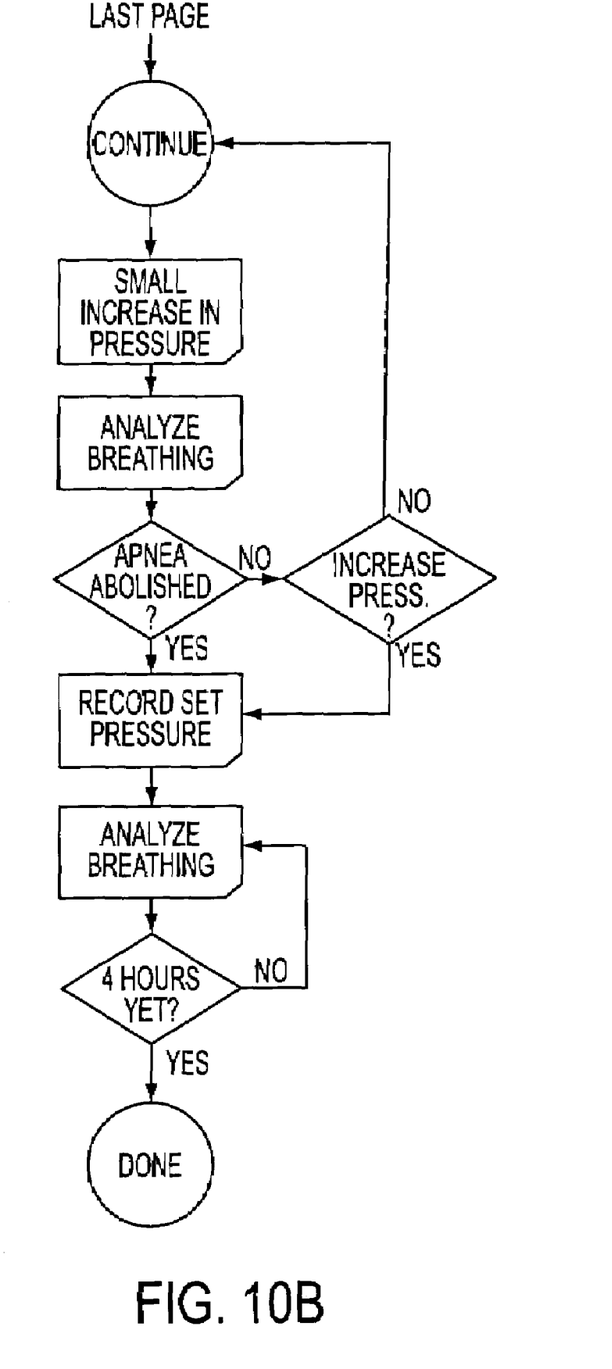

A more detailed discussion of the overall system operation will now be provided. FIGS. 10A through 10B show a general flow chart diagram of an exemplary system operation. After a patient is monitored and diagnosed by the sleep diagnostic system 10 for a first portion of the night, titration is performed for a second portion of the night. Such treatment can be administered in the privacy of the patient's home.

Initially, the system is powered for the assessment stage. The blower 12 is set to a minimum pressure, and an open command signal is sent to the valve 22 from the auto-CPAP or CPAP device. The controller 20 receives the open signal, and the valve 22 is actuated. The valve 22 is opened, and the controller 20 sends an acknowledgment indicating that the valve 22 has been successfully opened.

A timer is started and the breathing patterns of the patient are recorded. If the timing is less than a predetermined interval (i.e., four hours), then the timer continues until the predetermined interval is reached. During this time, the breathing patterns of the patient are monitored and recorded for later analysis. When the predetermined interval is reached, a close signal is sent to the controller 20 to close the valve 22. The valve 22 is then actuated and closed. The controller 20 sends an acknowledgment indicating that the valve 22 has been successfully closed.

If the diagnostic algorithm deems it appropriate, the air pressure in the mask 14 is slowly increased until signs of apnea ceases. This begins the titration stage.

The breathing patterns of the patient are analyzed. If apnea has not ceased, the air pressure is continually increased and the breathing patterns are further analyzed. This process continues until it is determined that apnea has ended (e.g., a minimum level or required therapeutic pressure is reached).

If apnea ceases, the final pressure is recorded and the breathing patterns are analyzed. If a predetermined interval (i.e., four hours) has not expired, although apnea has ceased, the breathing patterns are further analyzed. If the predetermined interval has expired, the system is powered off.

While the invention has been described in detail above, the invention is not intended to be limited to the specific embodiments as described. It is evident that those skilled in the art may now make numerous uses and modifications of and departures from the specific embodiments described herein without departing from the inventive concepts. For example, the invention can be implemented as a standard CPAP or auto-CPAP system having a blower that supplies breathing gas at a substantially constant pressure or as a bilevel CPAP system having a blower that varies the pressure of the breathing gas supplied in a cyclic manner to match the breathing pattern of the patient.

Further, the invention can be implemented without a valve member. The valve 22 can include a valve stopper and a valve body wherein one or more apertures are formed upstream along the length of the valve body. The apertures can have the same combined air flow resistance as a larger, single aperture. The valve stopper can include protrusions that are accommodated within the apertures. The controller 20 can control the operation (i.e., lowering or raising) of the valve stopper. When the apertures are opened, the conduit is partially occluded. In this instant, air flows through the apertures. When the apertures are closed, continuous positive airway pressure is provided to the patient.

The term "mask", as used herein, is meant to encompass any type of breathing appliance suitable for delivering a breathing gas to a patient as part of CPAP therapy. Some examples of suitable masks include, but are not limited to, cup-like masks that surround the nose and/or mouth of the patient, nasal cannulae with inserts that fit within the nostrils of the patient, and combinations of the foregoing.

The invention claimed is:

1. A breathing assistance system, comprising:
   a blower that provides a gas flow and can provide a continuous positive airway pressure;
   a respiratory interface;
   a conduit connected between said blower and said respiratory interface; and
   a valve disposed along said conduit between a first conduit portion a second conduit portion, said valve including an aperture formed in said conduit between said blower and said respiratory interface, and a valve member that pivots between:
   (a) a first, fully open position wherein the valve member partially occludes said conduit and allows gas flow through said aperture, the fully open position of said valve member providing a gas flow path directing said gas flow provided by said blower to pass from said first conduit portion into said second conduit portion to purge expired respiratory gases located in said second conduit portion through said aperture, and (b) a second position blocking said aperture so that continuous positive airway pressure is provided to a patient.

2. The system of claim 1, wherein said valve member is pivoted to said first position for diagnosing sleep apnea and said valve member is pivoted to said second position for treating sleep apnea.

3. The system of claim 1, further comprising a controller.

4. The system of claim 3, further comprising a signal line connected between said controller and said valve for conveying signals therebetween and allowing said controller to control the operation of said valve.

5. The system of claim 3, wherein said controller and said valve are positioned along the length of said conduit at spaced intervals, said valve located downstream of said controller.

6. The system of claim 3, wherein said controller and said valve are positioned between said blower and said respiratory interface at any location.

7. The system of claim 1, wherein said valve member is movable within said conduit between open and closed positions by means of an actuator.

8. The system of claim 1, wherein said valve member is movable by pneumatic actuation.

9. The system of claim 1, wherein said valve member is movable by solenoid actuation.

10. The system of claim 1, wherein said valve member is movable by motor actuation.

11. The system of claim 1, wherein said valve member is movable by electromagnetic actuation.

12. The system of claim 1, wherein said respiratory interface comprises a vent for purging expired respiratory gases.

13. A device for a breathing assistance system, said device comprising:

a valve disposed along a conduit between a first conduit portion and a second conduit portion, said valve including:

an aperture formed in said conduit between a blower and a respiratory a valve member that pivots between:

(a) a first, fully open position partially occluding said conduit and allowing wherein the valve member partially occludes said conduit and allows gas flow through said aperture, the fully open position of said valve member providing a gas flow path directing gas to flow from said first conduit portion into said second conduit portion to purge expired respiratory gases located in said second conduit portion through said aperture, and (b) a second position blocking said aperture so that continuous positive airway pressure is provided to a patient; and an actuator configured to receive an electrical control signal to control the rotational position of the valve member.

14. The device of claim 13, further comprising a controller for controlling the operation of said valve.

15. A method of diagnosing and treating sleep apnea during a sleep session using a system having a conduit and a valve, said method comprising the steps of:

pivoting the valve to a first position to partially occlude said conduit and allow air flow through an aperture;

maintaining the valve in the first position for a first portion of a sleep session such that continuous positive airway pressure is not provided to a patient during the first portion of the sleep session, the first portion of the sleep session having a predetermined duration;

monitoring the patient's breathing at least once during the first portion of the sleep session;

at the end of the first portion of the sleep session, pivoting the valve to a second position to block said aperture so that continuous positive airway pressure is provided to a patient; and maintaining the valve in the second position for a second portion of the sleep session such that continuous positive airway pressure is provided to the patient during the second portion of the sleep session.

16. The method of claim 15, wherein, in the monitoring step, a blower is set to a minimum pressure and the patient's breathing is recorded.

17. The method of claim 16, wherein an open command signal is sent to the valve to open the valve.

18. The method of claim 17, wherein, when the end of the predetermined duration is reached, a close signal is sent to close the valve.

19. The method of claim 15, wherein, in the providing step, continuous positive airway pressure is slowly increased.

20. The method of claim 19, wherein the patient's breathing is analyzed at least once during the second portion of the sleep session.

21. The method of claim 20, wherein, if apnea has not ceased in response to the continuous positive airway pressure, the continuous positive airway pressure is increased until apnea ceases, and the patient's breathing is analyzed.

22. The method of claim 21, wherein, when apnea ceases, the level of continuous positive airway pressure being provided to the patient is recorded and the patient's breathing is analyzed.

23. The method of claim 22, wherein the patient's breathing is further analyzed after apnea has ceased and before a predetermined interval has expired.

24. The method of claim 22, wherein, when a predetermined interval has expired, a blower is powered off.

25. The method of claim 15, wherein, in the providing step, the continuous positive airway pressure can be controlled by a blower or by a controller.

26. A method of diagnosing and treating sleep apnea in a single night using a system having a conduit with a valve, said method comprising the steps of:

partially occluding said conduit and allowing air flow through an aperture;

monitoring a patient's breathing for a first portion of the night;

blocking said aperture so that continuous positive airway pressure is provided to the patient; and providing continuous positive airway pressure for a second portion of the night, including:

increasing continuous positive airway pressure until an apnea ceases;

when the apnea ceases, analyzing the patient's breathing; and if a predetermined interval has not expired when the apnea ceases, continuing to analyze the patient's breathing for the remainder of the predetermined interval.

27. The method of claim 26, further including when the predetermined interval expires, powering off a blower.

28. A method, comprising:
during a first time period, partially occluding a gas conduit and allowing gas to flow through an aperture;
monitoring a patient's breathing at least once during the first time period; at the end of the first time period, blocking the aperture such that continuous positive airway pressure is provided to the patient;
providing continuous positive airway pressure to the patient during a second time period, including increasing the level of the continuous positive airway pressure until an apnea ceases;
at the end of the second time period, discontinuing providing continuous positive airway pressure to the patient; and
monitoring the patient's breathing at least once after the apnea ceases and before discontinuing providing continuous positive airway pressure to the patient.

29. A method according to claim 28, further comprising if the apnea ceases before the end of a predetermined interval, continuing to monitor the patient's breathing for the remainder of the predetermined interval.

30. A method, comprising:
delivering breathing gas through a conduit during a first time period and a second time period, the conduit associated with a system for delivering continuous positive airway pressure to a patient;
during the first time period, maintaining a valve associated with the conduit in a first position such that continuous positive airway pressure is not provided to the patient;
monitoring the patient's breathing at least once during the first time period; during the second time period, maintaining the valve in a second position such that continuous positive airway pressure is provided to the patient;
increasing the level of the continuous positive airway pressure until an apnea associated with the patient ceases; and
monitoring the patient's breathing at least once after the apnea ceases and before the end of the second time period.

31. A method for monitoring and treating sleep apnea during a sleep session, comprising:
maintaining a breathing assistance system coupled to a patient during both a first portion and a second portion of a sleep session, the first portion of the sleep session having a predetermined duration;
controlling the breathing assistance system such that continuous positive airway pressure is not provided to a patient during the first portion of the sleep session;
monitoring the patient's breathing at least once during the first portion of the sleep session;
at the end of the first portion of the sleep session, controlling the breathing assistance system to begin providing continuous positive airway pressure to the patient; and
providing continuous positive airway pressure to the patient during the second portion of the sleep session.

32. A method according to claim 31, wherein the breathing assistance system begins providing continuous positive airway pressure to the patient automatically at the end of the first portion of the sleep session, and not as a result of the monitoring of the patient's breathing.

33. A method according to claim 31, wherein:
the step of controlling the breathing assistance system such that continuous positive airway pressure is not provided to a patient during the first portion of the sleep session comprises moving a valve to a first position to allow gas flow provided by a blower to flow through an aperture; and
the step of controlling the breathing assistance system to begin providing continuous positive airway pressure to the patient comprises moving the valve to a second position to reduce or prevent gas flow through the aperture.

34. A method according to claim 31, further comprising:
delivering pressurized gas through a conduit coupled between a pressurized gas source and a patient interface during both the first and second portions of the sleep session;
during the first portion of the sleep session, allowing the pressurized gas to flow through one or more venting apertures such that continuous positive airway pressure is not provided to the patient; and
during the second portion of the sleep session, not allowing the pressurized gas to flow through the one or more venting apertures such that continuous positive airway pressure is provided to the patient.

* * * * *